United States Patent
Zhang

(10) Patent No.: US 11,925,434 B2
(45) Date of Patent: Mar. 12, 2024

(54) DEEP-LEARNT TISSUE DEFORMATION FOR MEDICAL IMAGING

(71) Applicant: SIEMENS HEALTHINEERS AG, Forchheim (DE)

(72) Inventor: Li Zhang, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 241 days.

(21) Appl. No.: 17/482,881

(22) Filed: Sep. 23, 2021

(65) Prior Publication Data

US 2022/0007940 A1 Jan. 13, 2022

Related U.S. Application Data

(62) Division of application No. 15/627,840, filed on Jun. 20, 2017, now Pat. No. 11,154,196.

(51) Int. Cl.
| | |
|---|---|
| *A61B 5/00* | (2006.01) |
| *G06T 3/00* | (2006.01) |
| *G06T 7/00* | (2017.01) |
| *G06T 7/30* | (2017.01) |
| *G06T 7/33* | (2017.01) |

(52) U.S. Cl.
CPC ............ *A61B 5/004* (2013.01); *A61B 5/0035* (2013.01); *A61B 5/0037* (2013.01); *G06T 7/30* (2017.01); *G06T 7/33* (2017.01); *G06T 7/337* (2017.01); *G06T 3/0068* (2013.01); *G06T 3/0093* (2013.01); *G06T 7/0016* (2013.01); *G06T 2207/30004* (2013.01)

(58) Field of Classification Search
CPC ........... G06T 3/0068; G06T 7/30; G06T 7/33; G06T 7/337; G06T 7/0016; G06T 2207/30004; G06T 3/0093; A61B 5/004; A61B 5/0035; A61B 5/0037
See application file for complete search history.

(56) References Cited

U.S. PATENT DOCUMENTS

| | | |
|---|---|---|
| 6,546,137 B1 | 4/2003 | Lai et al. |
| 2014/0119595 A1 | 5/2014 | Gallo et al. |
| 2016/0093048 A1 | 3/2016 | Cheng et al. |

FOREIGN PATENT DOCUMENTS

| | | |
|---|---|---|
| CN | 104268521 A | 1/2015 |

OTHER PUBLICATIONS

Cheng X., Zhang L., Zheng Y., "Deep similarity learning for multimodal medical images", MICCAI 2015 Deep Learning Workshop.

Mao Li et al., "Patient-specific biomechanical model as whole-body CT image registration tool", Medical Image analysis 22(2015) 22-34.

(Continued)

*Primary Examiner* — Chao Sheng

(57) ABSTRACT

A deep machine-learning approach is used for medical image fusion by a medical imaging system. This one approach may be used for different applications. For a given application, the same deep learning is used but with different application-specific training data. The resulting deep-learnt classifier provides a reduced feature vector in response to input of intensities of one image and displacement vectors for patches of the one image relative to another image. The output feature vector is used to determine the deformation for medical image fusion.

7 Claims, 2 Drawing Sheets

(56) References Cited

OTHER PUBLICATIONS

Oktay O., Zhang L., Mansi T., Mountney P., Mewes P., Nicolau S., Soler L., Chefd'hotel C., "Biomechanically driven registration of pre- to intra-operative 3D images for laparoscopic surgery", MICCAI 2013: 16 (Pt 2):1-9.

Papiez, B.W., Heinrich, M.P., Risser, L., Schnabel, J.A.: Complex lung motion estimation via adaptive bilateral filtering of the deformation field. In: MICCAI. (2013) 25-32.

Staring M., Klein S., Pluim, J.P.W., "A rigidity penalty term for nonrigid registration", Medical Physics 34, 4098 (2007).

A Survey Of Medical Image Registration; Maintz, et al. In Medical Image Analysis, Oxford University Press, vol. 2, No. 1, Jan. 1, 1998 (pp. 1-37).

Wu Guorong et al.: "Unsupervised Deep Feature Learning for Deformable Registration of MR Brain Images", Sep. 22, 2013 (Sep. 22, 2013), Medical Image Computing and Computer-Assisted; Intervention—MICCAI 2015 : 18th International Conference, Munich, Germany, Oct. 5-9, 2015; Proceedings; Springer International Publishing, CH.

Extended European Search Report (EESR) dated Sep. 24, 2018 in corresponding European patent application No. 18177763.2.

DEEP-LEARNT TISSUE DEFORMATION FOR MEDICAL IMAGING

CROSS-REFERENCE TO RELATED APPLICATIONS

This application is a Divisional of pending U.S. patent application Ser. No. 15/627,840, filed Jun. 20, 2017 which is incorporated herein by reference in its entirety.

BACKGROUND

The present embodiments relate to medical imaging. Medical images are fused together to assist in diagnosing and/or treating a patient. For medical image fusion, including mono-modality and multi-modality, deformable registration is commonly used to compensate for body position change, organ deformation, and/or cardiac, respiratory, and peristaltic motion between the images to be fused. A deformable registration first matches corresponding image structures by similarity measure, then warps one of the images based on either a physical or mathematical model to ensure the deformation is consistent with the actual human body change. Deformable registration may use elastic or fluid modeling, optical flow, bio-mechanical modeling, or diffeomorphism.

The deformable models attempt to make the deformations smooth across space so that adjacent parts do not have unrealistic movements relative to each other. Bio-mechanical properties may be applied to achieve realistic deformation for specific organs or structures. For example, for chest and abdomen registration, bi-lateral filtering allows sliding motion between lungs, diaphragm, liver, and rib cage. As another example, for spine registration, rigidity is formulated into the displacement update to avoid undesirable vertebra distortion. In yet another example, bio-mechanical modeling is used for liver surgery with insufflation.

These approaches are application specific. The approach for one type of tissue may not be generalized for other applications, resulting in different models or approaches for different applications. Moreover, these customized approaches may only address one specific aspect of the challenges of image fusion and may not be compatible with each other. For example, bi-lateral filtering and rigidity formulation are implemented based on different frameworks and cannot be applied together. Thus, for chest or abdomen registration, either sliding motion is allowed, or vertebra rigidity is ensured, but both features may not be achieved at the same time.

SUMMARY

By way of introduction, the preferred embodiments described below include methods, systems, instructions, and computer readable media for medical image fusion by a medical imaging system. A deep machine-learning approach is used. This one approach may be used for different applications. For a given application, the same deep learning is used but with different application-specific training data. The resulting deep-learnt classifier provides a reduced feature vector in response to input of intensities of one image and displacement vectors for patches of the one image relative to another image. The output feature vector is used to determine the deformation for medical image fusion.

In a first aspect, a method is provided for medical image fusion by a medical imaging system. A first medical image is divided into patches. For each patch, an input feature vector is extracted. The input feature vector includes intensities of the first medical image for the patch, a first displacement vector of the patch based on similarity with a second medical image, intensities of the first medical image for neighboring ones of the patches, and second displacement vectors of the neighboring patches based on similarity with the second medical image. A deep-learnt feature vector is determined from application of the input feature vector to a machine-learnt deep classifier. Non-rigid deformation of the first medical image relative to the second medical image from the deep-learnt feature vector is determined. The first medical image is fused with the second medical image based on the non-rigid deformation.

In a second aspect, a method is provided for medical image fusion by a medical imaging system. First and second sets of scan data representing a patient are acquired. Anatomy represented by the first set of scan data is deformed relative to anatomy represented by the second set of scan data. A deformation field aligning the anatomy of the first and second sets of scan data is determined with a machine-learnt deep neural network. A medical image is generated from the first and second sets of scan data and the deformation field.

In a third aspect, a system is provided for medical image fusion. At least one medical imaging system is configured to acquire first and second data representing a patient. Tissue represented in the first data displaced relative to the tissue represented in the second data. An image processor is configured to register the tissue of the first data with the second data by application of a deep-learnt neural network. A display is configured to display an image based on the registration.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Deep-learned tissue-specific deformation is provided for medical image fusion. A deep-learned deformation model may be used for different tissue properties. Such deep learning-based approaches may be applied to a board spectrum of applications without specific modification or redesign due to the generality and superior learning capability of the deep neural network. By changing the training data and not the approach to creating the model, deep-learned deformation models are provided for different applications.

In one embodiment, a deep-learned neural network estimates human body movement and deformation for medical image fusion. The approach may be generalized effectively and efficiently to different clinical cases. With the capability of processing a large amount of data from the deep neural network, satisfactory throughput in developing application specific models may be provided for unmet clinical needs.

Figure 1:
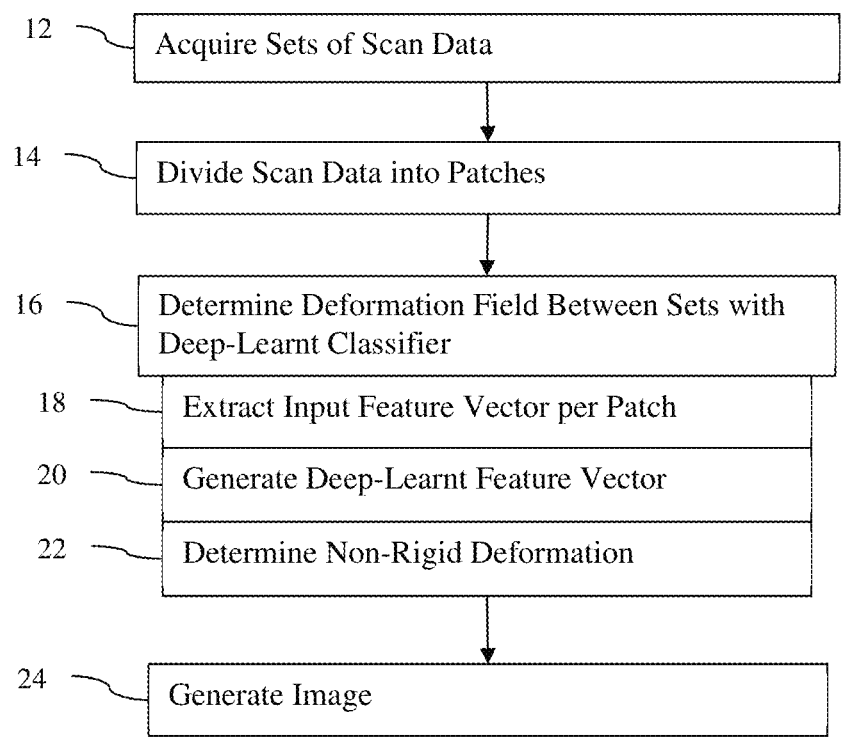
FIG. 1 is a flow chart diagram of one embodiment of a method for medical image fusion by a medical imaging system.

FIG. 1 shows a flow chart of one embodiment of a method for medical image fusion by a medical imaging system. To combine medical imaging from different times and/or with different modalities, the images are spatially registered. One image is deformed to account for distortions due to motion. The deformation for image fusion is based on deep machine-learnt classification.

Figure 4:
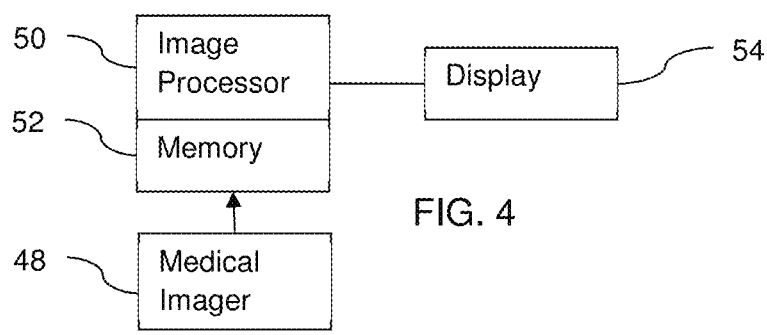
FIG. 4 is one embodiment of a system for medical image fusion.

The method is implemented by the system of FIG. 4 or another system. For example, act 12 is implemented with one or more medical imaging systems or scanners. Acts 12, 16 (including acts 18, 20, and 22) and 24 are implemented by an image processor, such as an image processor of a computed tomography (CT), magnetic resonance (MR), positron emission tomography (PET), ultrasound, single photon emission computed tomography (SPECT), x-ray, angiography, or fluoroscopy imaging system. As another example, the method is implemented on a picture archiving and communications system (PACS) workstation or implemented by a server. Other acts use interaction with other devices for registration and image fusion.

The acts are performed in the order shown (i.e., top to bottom or numerical order) or other orders. For example, act 12 is performed at different times for different images, so may be performed in part after act 14.

Additional, different, or fewer acts may be provided. For example, the method is performed using acts 12, 14, 16, and/or 24, but with different sub-acts (e.g., 18, 20, and/or 22). As another example, act 24 is not provided, but instead the registration is used to control or provide other feedback.

In act 12, one or more medical imaging scanners or systems acquire sets of scan data. The sets of scan data are acquired by scanning a patient. Alternatively, an image processor acquires the sets of scan data from one or more memories, databases, scanners, and/or via transfer over a computer network. Sets of scan data from previously performed scans are retrieved.

Each set is from a different time and/or modality. For example, one set of scan data is from a previous patient visit, such as weeks, months or years earlier. The same or different scanner scans the patient using the same or different settings at each visit. In another example, different modalities of scanners are used, such as CT or MRI for a preoperative scan and ultrasound or x-ray during an operation. Any type of scan data and corresponding modality of scanner may be used. Any of CT, x-ray, MR, ultrasound, PET, SPECT, fluoroscopy, angiography, or other scanner provides scan data representing a patient.

By using scan data from different times, changes over time may be viewed. By using different modalities, different types of tissue response may be provided. In image fusion from different modalities, the benefits of more than one modality may result. For example, one modality may have better resolution than another, but the other modality may provide information in real-time.

The tissue or anatomy represented in one set of scan data may be deformed relative to the tissue or anatomy representing in another set of scan data. For example, a location in one set of scan data may be of the lungs, but that location in another set is a bone. Due to the differences in time of acquisition and/or length of time to acquire, the different sets of scan data may be subject to different motion and corresponding position. Similarly, different imaging systems have different coordinate systems, so may provide different tissue at different locations. Physiological cycles (e.g., heart or breathing) may displace tissue in one set compared to another set. Patient and/or scanner motion may cause relative displacement. The relative displacement is rigid (i.e., the same for the entire frame of scan data) or non-rigid (i.e., affine where some locations are displaced by different amounts and/or directions than other locations).

The scan data, or medical imaging data, is a frame of data representing the patient. The data may be in any format. While the term "image" is used, the image may be in a format prior to actual display of the image. For example, the medical image may be a plurality of scalar values representing different locations in a Cartesian or polar coordinate format the same as or different than a display format. As another example, the medical image may be a plurality red, green, blue (e.g., RGB) values to be output to a display for generating the image in the display format. The medical image may be currently or previously displayed image in the display format or other format.

The scan data or image represents a volume of the patient. The patient volume includes all or parts of the patient. The volume and corresponding scan data represent a three-dimensional region rather than just a point, line or plane. For example, the scan data is reconstructed on a three-dimensional grid in a Cartesian format (e.g., N×M×R grid where N, M, and R are integers greater than one). Voxels or other representation of the volume may be used. The scan data or scalars represent anatomy or biological activity, so is anatomical and/or functional data. Alternatively, the scan data represents a two-dimensional region or plane within the patient.

In act 14, the image processor divides one of the medical images into patches. The scan data of one set representing the patient is divided. For example, a set of scan data represented a volume of the patient is divided into the patches where each patch represents a different sub-volume of the volume. The other image is not divided, but may be.

Figure 2:
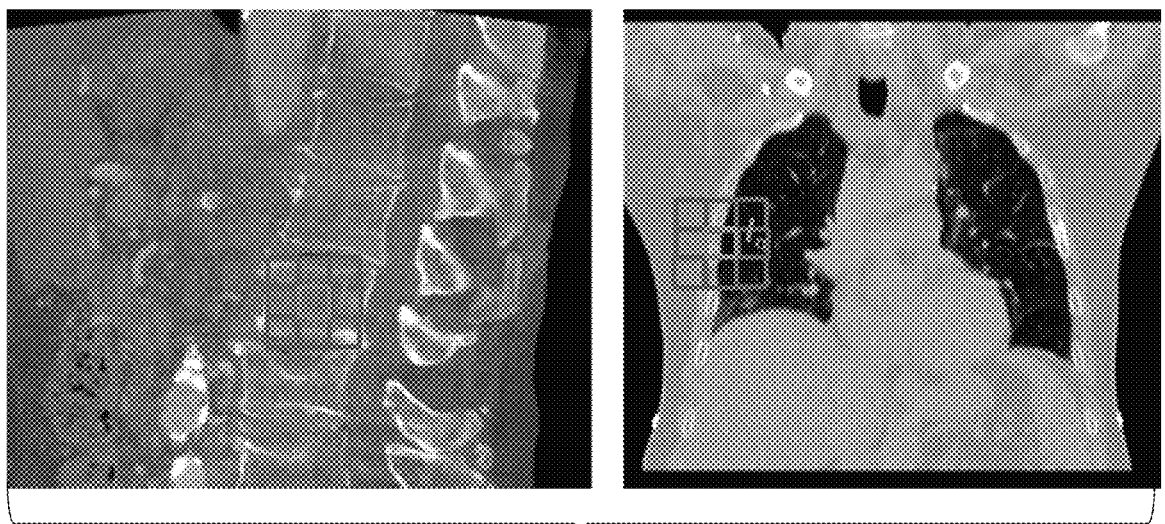
FIG. 2 illustrates example patches in example medical images.

The division is by forming separate images or sets for the patches. Alternatively, a group or patch membership map is created assigning different locations to respective patches. Each voxel or pixel may be labeled as belonging to a respective patch. FIG. 2 shows two different example two-dimensional medical images. Each image includes 9 patches as examples shown as square boxes. The entirety or a larger portion of each image is divided into patches.

Any patch size may be used, such as 16×16×16 voxels. Anisotropic patch sizes may be used, such as 12×18 pixels. The size of the patches is the same throughout the entire image, but may vary through the image (e.g., larger patch sizes for background or larger regions of continuous tissue type).

The patches provide for non-rigid deformation determination. A displacement vector of the deformation for image fusion is estimated for each patch. For a realistic deformation, the displacement vector of a patch is not only related to its own points, but also the points in its neighboring patches. For example, in FIG. 2, the patch $I_p$ (i.e., center patch in the 9 patches shown) in the left image is in the middle of the vertebra and will move together with most of its neighboring patches because the neighbor patches belonging to a same rigid vertebra. The patch $I_q$ (i.e., center patch in the 9 patches shown) in the right image is located at the boundary of the lung, so the left part of the patch will move together with the patches in the rib cage while the right part will move together with the patches in the lung.

Referring again to FIG. 1, the image processor determines a deformation field aligning the anatomy of the sets of scan data in act 16. Displacements of tissue or anatomy for one image relative to another image indicates the alterations to align or correct for the deformation. For non-rigid deformation, the deformation field provides a displacement vector (e.g., magnitude and direction) for each patch. This collection of displacement vectors represents the deformation between the medical images. Higher resolution deformation is provided by using smaller patches. The deformation field may be provided by voxel or pixel. For rigid deformation or miss-alignment, each vector of the deformation field is the same, so may be represented by a single displacement vector.

The determination uses a machine-learnt deep neural network or classifier. Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. Hierarchical structures are employed, either for learning features or representation or for classification or regression.

Figure 3:
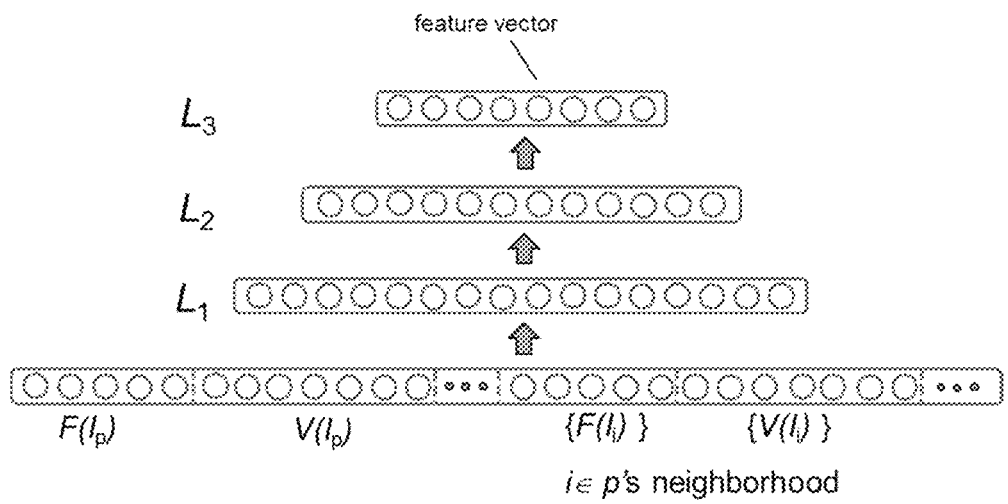
FIG. 3 illustrates layers of an example deep machine-learnt classifier.

The deep machine-learnt classifier learns filter kernels or other features that indicate the deformation or may be used to determine deformation. Rather than or in addition to outputting the deformation, features useable to determine the deformation are learned using deep learning. For example, FIG. 3 shows an input feature vector as the lower row with the deep machine-learnt classifier having at least three layers ($L_{1-3}$) with the last layer ($L_3$) outputting a feature vector that may be used to determine the deformation field.

The deep machine learning uses training data. The training data provides pairs of images and the known or ground truth deformation field between each pair. Patches, images, and ground truth may be provided. Any number of such examples are provided, such as hundreds or thousands. The ground truth examples are provided based on expert input (e.g., radiologists provided deformation fields, input of landmarks, or segmentation), based on automated landmark or segmentation in the images, based on application of a registration algorithm designed for the specific application, from one or more clinical studies, and/or from one or more databases.

The training data is for a specific application. For example, the anatomy of interest and/or the types of images to be fused provides the application (e.g., an anatomic imaging application). For example, a lung cancer application may use x-ray or CT images from different times. As another example, a liver application may use an MR or CT image with a SPECT or PET image. A given application may include any number of types of tissue. The deep learning is performed for the specific application. Alternatively, training data form multiple applications is used to train the classifier for dealing with different applications.

In one embodiment, the same input feature vector and/or deep learning neural network layer configuration is used for training classifiers for different applications or regardless of the anatomic imaging application. For medical image registration, especially deformable registration, approaches customized to accommodate underlying anatomic structure properties for particular applications may be avoided. Instead, the deep learning-based approach is generalized to many or all applications where the application-specific training data may vary by application. The machine learning deals with the anatomic structure properties rather than introducing limitations or constraints in an application specific algorithm. The deep learning approach may decrease the development time for a given application and generates robust and accurate outputs.

Given the training data, the deep learning learns the feature vector that distinguishes between different deformations. One or more filter kernels that may be convolved with the input feature vector to provide a feature vector output for a patch are learnt. Max pooling, connectivity, and/or other operations may be included. The deep leaning provides a deep machine-learnt classifier that outputs the results of convolution of the filter kernel or kernels and/or other operations with the input. The results are the feature vector for the patch.

Any input feature vector may be used for the training and application of the deep machine-learnt classifier. For example, the intensities (i.e., scalar or RGB values of voxels or pixels) of the patch are input. As another example, Haar wavelets or other filtering results applied to the intensities are used. In yet another example, a displacement vector of the patch to best match the other image is calculated and input as part of the input feature vector. A map of measures of similarity for different displacements of the patch (e.g., measure of similarity for each of a set of displacements) may be used. Alternatively or additionally, the similarity map is of displacements relative to the other image of different voxels in the patch. The similarity map includes any number of displacements. In one embodiment, combinations of input features are used, such as the intensities and the displacement vector or map of measures of similarity.

In one embodiment, the input feature vector for the patch includes information from neighboring patches. For example, the intensities and/or displacement vectors for the neighboring patches are included. The information from the neighboring patches is the same or different type of information as for the patch itself.

Acts 18, 20, and 22 represent one embodiment of determining the deformation field with the deep machine-learnt classifier. Acts 18, 20, and 22 are performed for each patch. The collection of displacement outputs for the patches provides the deformation field. Additional, different, or fewer acts may be provided.

In act 18, an input feature vector is extracted for each patch. The extraction is by look-up, image processing, receipt, mining, searching, or other data gathering. For example, the extraction is by image processing using the images, one image to be deformed to the other image.

To estimate the displacement vector for each patch $I_p$, the input for the deep neural network is a concatenated vector of different features. Values for various features are collected or concatenated. In one embodiment, the input is patch intensities, patch displacement, neighbor patch intensities, and neighbor patch displacements. FIG. 3 shows an example of this embodiment. The lower row represents the input feature vector. Other input feature vectors may be used.

The input feature vector includes intensities of one medical image for the patch. In FIG. 3, the scalar or other value for each pixel or voxel in the patch is an intensity map $F(I_p)$ for the patch, $I_p$. The intensities for patches from both medical images may be used in alternative embodiments.

The input feature vector includes one or more displacement vectors for the patch. The displacement of the patch of one image to provide a best or sufficient match with the other image is determined. The patch is displaced by translation along different dimensions. Rotation and/or scale displacement may also be used. The magnitude (amount) of translation displacement, angle of the translation displacement, amount of rotation, direction of rotation, amount of scale change, and/or direction of scale change are determined.

The similarity of the patch to the other image with different offsets is tested. The displacement vector for the offset with a best or sufficient match or measure of similarity is selected. A threshold may be used for sufficiency.

Any search pattern may be used to determine the best or sufficient match. For example, a random search, search over a regular pattern, coarse to fine search, and/or a search based on feedback from other displacements is used. A starting displacement for the search may be based on a displacement from a neighboring patch or a rigid displacement calculated between the two images.

Any measure of similarity may be used. For example, cross correlation, mutual information, K-L distance, or minimum sum of absolute differences is used. In another example, the measurement of similarity is obtained by applying another machine-learnt classifier. The machine learns to distinguish similar from dis-similar. Any machine learning may be used, such as a deep learned similarity measure.

The displacement vectors from similarity matching are directly obtained from the similarity measure that links the correspondences between the patch and the image and therefore are not modeled with desired properties (e.g., smoothness constraints). The similarity measure may be robust to noise in the images.

In one embodiment, the displacement vector for each or for a sub-set of locations in the patch is found. This results in a collection of displacement vectors for a given patch. This collection is a similarity matching map $V(I_p)$ of $I_p$ shown in FIG. 3. In alternative embodiments, one displacement vector for the patch is used in the input feature vector.

The input feature vector for a given patch may include information for one or more neighboring patches. For example, information is used for all directly adjacent neighborhood patches. In the examples of FIG. 2, there are eight directly adjacent neighborhood patches for patch $I_p$ or $I_q$. For a volume, there may be 26 directly adjacent neighborhood patches. Information from fewer than all directly adjacent patches may be used, such as only four (up, down, left, and right) for the examples of FIG. 2. Information from other neighbor patches spaced from the patch by one or more other patches may be used. For patches at an edge of the scan plane or volume, there may be fewer neighborhood patches.

For the neighboring patches, the same or different type of information as the patch of interest is used. For example, the intensities and displacement vector or similarity matching maps for each of the neighbor patches are included in the input feature vector. In the example of FIG. 3, the intensity maps for the neighboring patches are represented as: $\{F(I_i) | i \in p\text{'s neighborhood}\}$, and the displacement vectors in similarity matching maps for the neighboring patches are represented as: $\{V(I_i) | i \in p\text{'s neighborhood}\}$ of $I_p$'s neighboring patches $I_i$. Different, additional, or less information from neighboring patches may be included, such as different types of information from different neighboring patches.

In act 20 of FIG. 1, the image processor generates a deep-learnt feature vector from application of the input feature vector to the deep-learnt classifier. The machine training of the deep neural network is an unsupervised learning approach. The high dimensional input feature vector of the patch and neighbor patches intensity and similarity matching maps is reduced to a feature vector with lower dimension (i.e., amount of data or number of values). FIG. 3 shows layer $L_3$ as providing the output feature vector, but other layers with or without one or more intervening layers reducing data may be used. The deep machine-learnt classifier outputs the deep-learnt feature vector in response to input of the input feature vector.

The values of the input feature vector are applied to the deep machine-learnt classifier. The layers of the deep machine-learnt classifier convolve and/or otherwise process the input information to determine values for the output feature vector.

In act 22, the image processor determines non-rigid deformation of the medical image relative to the other medical image from the deep-learnt feature vectors. The values of the output feature vector for the patch are used to determine the deformation between the images.

The deformation local to the patch is determined. A displacement in translation, rotation, and/or scale is determined. Separate deformation determinations for each patch may be used to determine the deformations throughout the image. The collection of deformations from the various patches provides a non-rigid deformation field for altering the medical image or scan data to the arrangement or anatomical distribution of the other medical image or scan data.

There are various techniques to determine the deformation from the values of the output feature vector. One technique is used. More than one technique may be used and the results combined, such as averaging the displacements for the same patches in the displacement field.

In one technique, the deformation is determined as a further output of the deep-learnt classifier. During the unsupervised training of the deep neural network or other classifier, the known ground truth of the deformation is related to the output feature vector. The classifier may use the values of the output feature vector to determine the deformation (e.g., a displacement vector for the patch).

In another technique, a look-up is performed. The values of the deep-learnt feature vector are matched with a database of training deformations with known deformations. The samples of the database are indexed by values of the output feature vector for the samples. Using Euclidean distance or other matching, a sample with the best match is found. The deformation associated with this sample is assigned as the deformation for the patch. For an input patch in a query image, the output feature vector is matched to a particular training patch with known ground truth deformation fields using the feature vector.

In yet another technique, clustering is used. The values of the deep-learnt feature vector are fit to one of a plurality of clusters. The output feature vectors for all the training patches are grouped by an unsupervised clustering method such as K-mean or hierarchical clustering. Then, the output feature vector of a patch is clustered into a group or cluster. The values of the output feature vector are used to determine membership in one of the clusters. Each cluster is associated with a deformation or displacement. The displacement of the fit cluster is assigned to the patch.

By determining the displacement or deformation for each patch in an image, the deformation field for that image is determined. This deformation field is a non-rigid deformation. In an alternative embodiment, a rigid registration is determined. The deformation or displacement for all the patches is the same (i.e., one displacement is provided). The displacements from the patches are averaged, the values for the output feature vectors from all the patches are used together to find one displacement, or another approach is used to find the rigid displacement. In other embodiments, sub-sets of patches rigidly deform. For example, the patches are labeled as belonging to a same body part (e.g., head, arm, hand, leg, or feet). Based on joint location, the patches of the body part move together. The deformation for that body part is constrained to be rigid. The rigid registration parameters for these body parts are closely related to the conjunct body structures. The deep machine training may learn and predict the rigid deformation. In the rigid registration case, the input of the network is the same, but the output is the rigid registration parameters. The deformations for different body parts in a same image may be different, so non-rigid deformation is provided for the image.

In act 24, the image processor generates a medical image. The medical image is generated from both component medical images using the deformation field. The generated image includes information from both scan sets of data. To avoid deformations resulting in different anatomy being represented at a same location, one of the images is deformed to the other image. The deformation field is applied to one of the images or sets of scan data, warping the scan data with the non-rigid deformation. The deformation aligns the anatomical structures of the sets of scan data, so that pixels or voxels at the same locations represent the same anatomy. The scan data may then be combined into the fused medical image.

Any type of medical image fusion may be used. For example, a three-dimensional rendering is performed from preoperative or other scan data. Scan data from an intraoperative scan is used to generate an overlay or aligned adjacent view. The fused image may include adjacent but separate visual representations of information from the different sets of scan data. The registration is used for pose and/or to relate spatial positions, rotation, and/or scale between the adjacent representations. In another example, an image is displayed from one set of scan data and a color overlay is generated from another set of scan data. In yet another example, the sets of scan data are combined (e.g., averaged) prior to rendering and then the fused image is rendered from the combined data. Any now known or later developed fusion may be used.

The fused image is displayed. The image is displayed on a display of a medical scanner. Alternatively, the image is displayed on a workstation, computer, or other device. The image may be stored in and recalled from a PACS memory.

FIG. 4 shows one embodiment of a system for medical image fusion. The system determines a spatial relationship between images from different scanners, settings, and/or times. The deformation of the tissue or anatomy represented in one image relative to the other is determined, allowing fusion of information from different images.

The system implements the method of FIG. 1. Other methods or acts may be implemented.

The system includes a medical imaging system 48, a memory 52, an image processor 50, and a display 54. Additional, different, or fewer components may be provided. For example, a network or network connection is provided, such as for networking with a medical imaging network or data archival system. In another example, a user interface is provided for interacting with the image processor 50 and/or the medical imaging system 48. As another example, more than one medical imaging system 48 is provided.

The image processor 50, memory 52, and/or display 54 are part of the medical imaging system 48. Alternatively, the image processor 50, memory 52, and/or display 54 are part of an archival and/or image processing system, such as associated with a medical records database workstation or server. In other embodiments, the image processor 50, memory 52, and display 54 are a personal computer, such as desktop or laptop, a workstation, a server, a network, or combinations thereof. The image processor 50, display 54, and memory 52 may be provided without other components for acquiring data by scanning a patient (e.g., without the medical imaging system 48).

The medical imaging system 48 is a medical diagnostic imaging system. Ultrasound, CT, x-ray, fluoroscopy, PET, SPECT, and/or MR systems may be used. Other medical imaging systems may be used. The medical imaging system 48 may include a transmitter and includes a detector for scanning or receiving data representative of the interior of the patient.

One medical imaging system 48 is shown. The different sets of data may be acquired by scanning the patient with this one medical imaging system 48 at different times and/or with different settings. Alternatively, different medical imaging systems 48 of a same type scan the patient at different times. In other embodiments, multiple medical imaging systems 48 are provided. Each medical imaging system 48 is of a different modality or different type of a same modality. By scanning at the same or different times with the different medical imaging systems 48, different sets of data representing the patient are acquired.

Due to the differences in time, modality, settings, and/or period of scanning, tissue, anatomy, or objects represented in one set of data may be displaced relative to the representation in another set of data. This deformation is to be corrected for generating an image using information from both sets of data.

The memory 52 is a graphics processing memory, a video random access memory, a random access memory, system memory, cache memory, hard drive, optical media, magnetic media, flash drive, buffer, database, combinations thereof, or other now known or later developed memory device for storing scan or image data. The memory 52 is part of the medical imaging system 48, part of a computer associated with the image processor 50, part of a database, part of another system, a picture archival memory, or a standalone device.

The memory 52 stores the scan or image data. Sets or frames of data from different times, modes, settings, and/or periods of scanning are stored. For example, data from the medical imaging system 48 acquired at different times for a same patient is stored. The data is in a scan format or reconstructed to a volume or three-dimensional grid format.

The memory 52 stores other information used in the registration. For example, the values of the input feature vector, the values of the output feature vector, the matrix or matrices of the deep machine-learnt classifier, patch information, and/or displacement vectors (e.g., non-rigid deformation or transform) are stored. The image processor 50 may use the memory 52 to temporarily store information during performance of the method of FIG. 1.

The memory 52 or other memory is alternatively or additionally a non-transitory computer readable storage medium storing data representing instructions executable by the programmed image processor 50 for fusion imaging. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 50 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining deformation between two images and/or fusion imaging. The image processor 50 is a single device or multiple devices operating in serial, parallel, or separately. The image processor 50 may be a main processor of a computer, such as a laptop or desktop computer, or may be a processor for handling some tasks in a larger system, such as in the medical imaging system 48. The image processor 50 is configured by instructions, firmware, design, hardware, and/or software to perform the acts discussed herein.

The image processor 50 is configured to register the tissue or objects of one set of data with tissue or objects of another set of data by application of a deep-learnt neural network. An input feature vector is created from the data. For example, the intensities of both images or patches of one or both images are used. In another example, intensities of patches from one image and similarity maps or displacement vectors of the patches relative to another image are input as the feature vector.

The image processor 50 is configured to output a feature vector based on applying the input feature vector to the deep-learnt neural network. For example, given intensities and displacement vectors for patches of one set of data relative to another set of data, the deep-learnt neural network provides an output feature vector. The output feature vector for each patch is used to determine the displacement for that patch. The deformation field resulting from the various patches provides the transform registering the sets of data to each other.

The image processor 50 is configured to warp one set of data relative to the other set of data based on the transform. Interpolation, extrapolation, and/or filtering may be used to transition the deformation between centers of the patches. The deformation is corrected, allowing fusion of the sets of data. A fusion image, such as an image showing anatomy from one set with an overlay from another set or such as two representations of anatomy from the two sets shown at a same time in one image, is generated.

The display 54 is a monitor, LCD, projector, plasma display, CRT, printer, or other now known or later developed devise for outputting visual information. The display 54 receives images, graphics, text, quantities, or other information from the image processor 50, memory 52, or medical imaging system 48.

One or more medical images are displayed. The images use the registration. An image based on the registration is shown, such as showing a fusion image. The fusion image may assist in diagnosis and/or treatment. For diagnosis, change over time or different types of information for the same spatial locations or anatomy are provided, giving the physician more spatially accurate information. For treatment, the change over time or real-time guidance from one mode with detail or planning information from another mode as spatially aligned assists in applying treatment to the correct location in the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for medical image fusion by a medical imaging system, the method comprising:
   acquiring first and second sets of scan data representing a patient with anatomy represented by the first set of scan data deformed relative to anatomy represented by the second set of scan data;
   determining a deformation field aligning the anatomy of the first and second sets of scan data with a machine-learnt deep neural network, the machine-learnt deep neural network outputting the deformation field; and
   generating a medical image from the first and second sets of scan data and the deformation field.

2. The method of claim 1 wherein acquiring comprises acquiring the first and second sets of scan data with a same modality of scanner at different times or with different modalities of scanners.

3. The method of claim 1 further comprising dividing the first set of scan data into patches, wherein determining the deformation field comprises determining from intensities and displacements for the patches of the first set of scan data relative to the scan data of the second set.

4. The method of claim 3 wherein determining comprises determining, for each of the patches, from intensities and displacements for the patch and for neighboring patches.

5. The method of claim 3 wherein determining comprises determining with a feature vector output by the machine-learnt deep neural network.

6. A system for medical image fusion, the system comprising:
   at least one medical imaging system configured to acquire first and second data representing a patient, tissue represented in the first data displaced relative to the tissue represented in the second data;
   an image processor configured to register the tissue of the first data with the second data by application of a deep-learnt neural network, the deep-learnt neural network configured to output displacements; and
   a display configured to display an image based on the registration.

7. The system of claim 6 wherein the image processor is configured divide the first data into patches and to register based on an output feature vector from the deep-learnt neural network given intensities and displacement vectors for the patches of the first data relative to the second data.

\* \* \* \* \*